(12) United States Patent
Stolte et al.

(10) Patent No.: US 6,788,396 B2
(45) Date of Patent: Sep. 7, 2004

(54) DETERMINATION OF OPTICAL PROPERTIES OF A DEVICE UNDER TEST IN TRANSMISSION AND IN REFLECTION

(75) Inventors: Ralf Stolte, Hamburg (DE); Patrick Ziegler, Boblingen (DE)

(73) Assignee: Agilent Technologies, Inc., Palo Alto, CA (US)

( * ) Notice: Subject to any disclaimer, the term of this patent is extended or adjusted under 35 U.S.C. 154(b) by 9 days.

(21) Appl. No.: 10/179,368

(22) Filed: Jun. 25, 2002

(65) Prior Publication Data

US 2003/0020900 A1 Jan. 30, 2003

(30) Foreign Application Priority Data

Jul. 27, 2001 (EP) ............................................. 01118179

(51) Int. Cl.[7] .............................................. G01N 21/00
(52) U.S. Cl. ..................................................... 356/73.1
(58) Field of Search ........................ 356/73.1, 364–370, 356/450–469, 433, 434; 250/214 R, 225, 340, 341.1–341.8

(56) References Cited

U.S. PATENT DOCUMENTS

| 4,304,489 A | 12/1981 | Wakabayashi et al. ...... 356/73.1 |
| 5,268,741 A | 12/1993 | Chou et al. .................. 356/351 |
| 5,365,335 A | 11/1994 | Sorin .......................... 356/345 |
| 5,764,348 A | 6/1998 | Bloom ........................ 356/73.1 |
| 6,252,222 B1 * | 6/2001 | Kasapi et al. ........... 250/214 R |

FOREIGN PATENT DOCUMENTS

| EP | 1 014 033 | 6/2000 |
| EP | 1 113 250 | 7/2001 |
| WO | WO 01/20289 | 3/2001 |

OTHER PUBLICATIONS

Froggatt, M. et al., "Full Complex Transmission and Reflection Characterization . . . ".
Sandel et al., "Optical Network Analysis and Longitudinal Structure Charactrization of Fiber Bragg Grating," Dec., 1998, IEEE, Journal of Lightwave Technology, vol. 16, No. 12.
Sandel et al., "Optical Network Analyzer Applied for Fiber Bragg Grating Characterization," Sep. 1997, IEEE.
Tabellion, M., Examiner, European Search Report, Application No. EP 01 11 8179, dated Dec. 17, 2001.
U.S. patent application Ser. No. 10/179,347, Stolte et al., filed Jun. 25, 2002.

* cited by examiner

Primary Examiner—Tu T. Nguyen

(57) ABSTRACT

The present invention relates to determination of optical properties, e.g. polarization dependent loss (PDL), polarization mode dispersion (PMD), differential group delay (DGD), insertion loss, return loss and/or chromatic dispersion (CD), of a device under test (DUT) in transmission and in reflection of an optical beam. The invention is disclosing an element that is at least partly transmissive and at least partly reflective.

10 Claims, 6 Drawing Sheets

DETERMINATION OF OPTICAL PROPERTIES OF A DEVICE UNDER TEST IN TRANSMISSION AND IN REFLECTION

BACKGROUND OF THE INVENTION

The present invention relates to determination of optical properties, e.g. polarization dependent loss (PDL), polarization mode dispersion (PMD), differential group delay (DGD), insertion loss, return loss and/or chromatic dispersion (CD), of a device under test (DUT) in transmission and in reflection of an optical beam.

Measurement setups for the above-mentioned purpose shall be as easy to handle as possible and shall reveal all optical properties of the DUT as fast as possible and with as little handling as possible. This means that the DUT should be fully characterized to all parameters required when it is once connected to the measurement setup. For a full characterization it is required to measure all parameters both in transmission and in reflection as fast as possible.

From the disclosure of work of Sandel et al (David Sandel, Reinhold Noé, "Optical Network Analyzer applied for Fiber Bragg Grating Characterization", ECOC 97, 22–25 Sep. 1997, Conference Publication No. 448, © IEE, 1997, pp. 186–189; David Sandel et al, "Optical Network Analysis and Longitudinal Structure Characterization of Fiber Bragg Grating", Journal of Lightwave Technology, Vol. 16, No. 12, December 1998, pp. 2435–2442) it is known a method for polarization-resolved optical fiber Bragg grating characterization. However, in these disclosures only the reflection of the DUT is measured.

From a work of Froggatt at al (Froggatt et al, "Full Complex Transmission and Reflection Characterization of a Bragg Grating in a Single Laser Sweep",) it is known to use a measurement setup to measure the group delay of a DUT in transmission and in reflection in both directions. However, with the disclosed measurement setup it is not possible to measure PMD or PDL. Moreover, the measurement setup disclosed in this article causes problems because the detectors used to detect the signals of reflection and transmission receive the signals of both directions simultaneously, i.e. the reflected signal of one direction is superimposed with the transmitted signal of the other direction and the transmitted signal of one direction is superimposed with the reflected signal of the other direction. Therefore, complex measures are necessary to distinguish between these signals without really knowing all impacts of this superposition of signals.

SUMMARY OF THE INVENTION

Therefore, it is an object of the invention to provide improved determination of optical properties of a DUT in one direction in transmission and in reflection of an optical beam.

The object is solved by the independent claims.

An advantage of the present invention is the provision of a fast way to convert a measurement setup of the above-mentioned art for measuring in transmission into a measurement setup which is able to measure the DUT in one direction in transmission and in reflection, simultaneously. In a preferred embodiment of the invention the inventive element comprises a semi-transparent mirror. This embodiment is easy to fabricate, easy to handle and cheap in production costs.

In a further preferred embodiment of the invention the element has a known proportion of transmission and reflection, more preferred also known optical properties, e.g. PDL, PMD, DGD, insertion loss, return loss, CD. It is preferred to have an element with substantially no PMD, DGD, insertion loss, return loss, PDL, and CD in the relevant wavelength range.

It is further preferred that the element is prepared in such a way that the optical properties can be adjusted. This embodiment guarantees more flexibility when using the inventive element.

In another preferred embodiment of the invention the element comprises a first beam splitter or coupler in an initial path of the beam for coupling out at least a part of the beam into a first path, an optical guide for guiding the part of the beam partly back into the initial path in reverse direction, the guide preferably comprising a second beam splitter or coupler in the first path for coupling the part of the beam back into the initial path. This embodiment realizes the invention without the necessity of using a semi-transparent mirror.

In another preferred embodiment of the invention the element comprises a first beam splitter or coupler in an initial part of the beam for coupling out at least part of the beam Into a first path, a mirror in the first path for reflecting back the part of the beam to the first beam splitter so that the first beam splitter partly guides the part back into the initial path in reverse direction and partly into a second path guiding the reflected signal in the initial direction.

Other preferred embodiments are shown by the dependent claims.

It is clear that the Invention can be partly or entirely embodied or supported by one or more suitable software programs, which can be stored on or otherwise provided by any kind of data carrier, and which might be executed in or by any suitable data processing unit.

BRIEF DESCRIPTION OF THE DRAWINGS

Other objects and many of the attendant advantages of the present invention will be readily appreciated and become better understood by reference to the following detailed description when considering in connection with the accompanied drawings. The components in the drawings are not necessarily to scale, emphasis instead being placed upon clearly illustrating the principles of the present invention. Features that are substantially or functionally equal or similar will be referred to with the same reference sign(s).

DETAILED DESCRIPTION OF THE INVENTION

With regard to propagation of light, a single device may often perform functions of both, or either of, beam splitting and coupling. For example, light entering a first port of such a device can be split into two paths such that a portion of the light exits via a second and a portion of the light exits via a third port. Conversely, light entering the device via the second port and light entering the device via the third port can be coupled together and exit the device via the first port. The term "coupler" is used herein for a device that performs either of coupling or beam splitting, or both of coupling and beam splitting.

Figure 1:
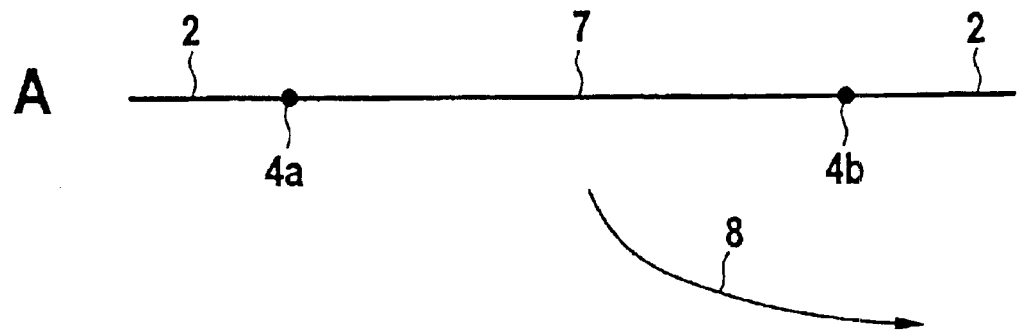
FIG. 1 shows a principle of an embodiment of the inventive method.
Figure 1:
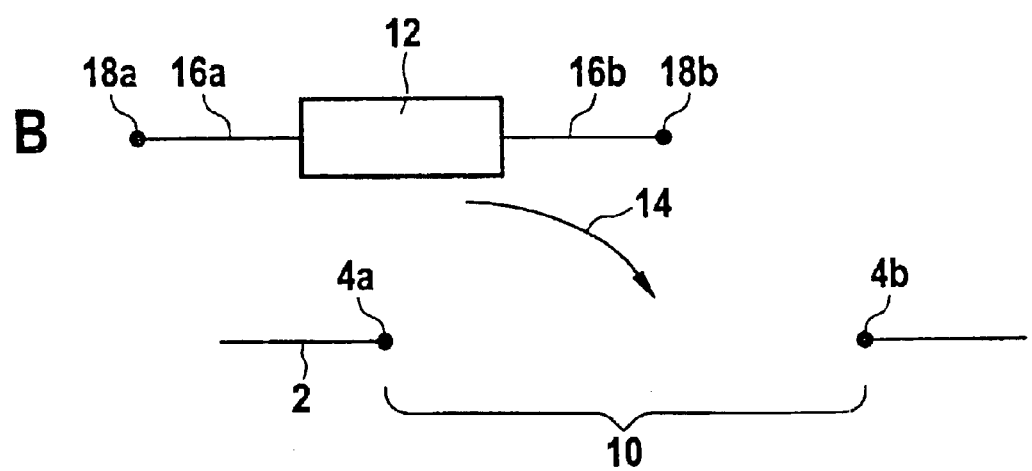
Figure 1:
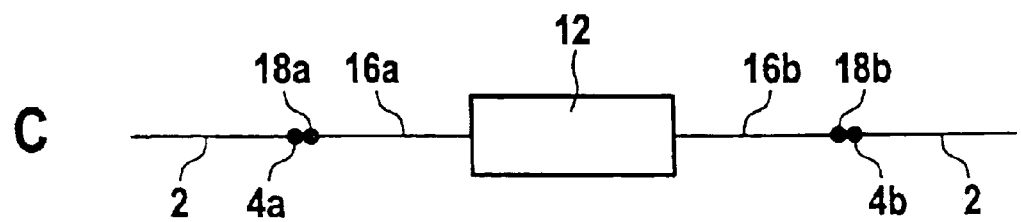

Referring now in greater detail to the drawings, FIG. 1 shows schematically, a principle of an embodiment of the inventive method. In step A of FIG. 1, there is shown a reference arm 2 of a measurement setup 400 (see FIG. 5) for determination of optical properties of a DUT 6 (FIG. 5) in transmission and in reflection in one direction. Such a measurement setup 400 can be calibrated and/or verified by a calibration and/or verification element, as disclosed in U.S. patent application Ser. No. 10/179,347, filed Jun. 25, 2002, which is incorporated herein by reference.

Reference arm 2 has two connectors 4a and 4b. Between connectors 4a and 4b, a patch-cord 7 is inserted. By releasing a connection at connectors 4a and 4b (indicated by an arrow 8) it is possible to disconnect patch-cord 7 from reference arm 2. This, as shown in step B of FIG. 1, opens a gap 10 between connectors 4a and 4b. This makes it possible to insert an element 12 into gap 10 (indicated by an arrow 14). For this purpose, element 12 is prepared with two short patch-cords 16a and 16b having connectors 18a and 18b, which can be connected to connectors 4a and 4b of reference arm 2, respectively. As shown in step C of FIG. 1, as a result, element 12 is inserted in reference arm 2 and has replaced patch-cord 7.

Figure 2:
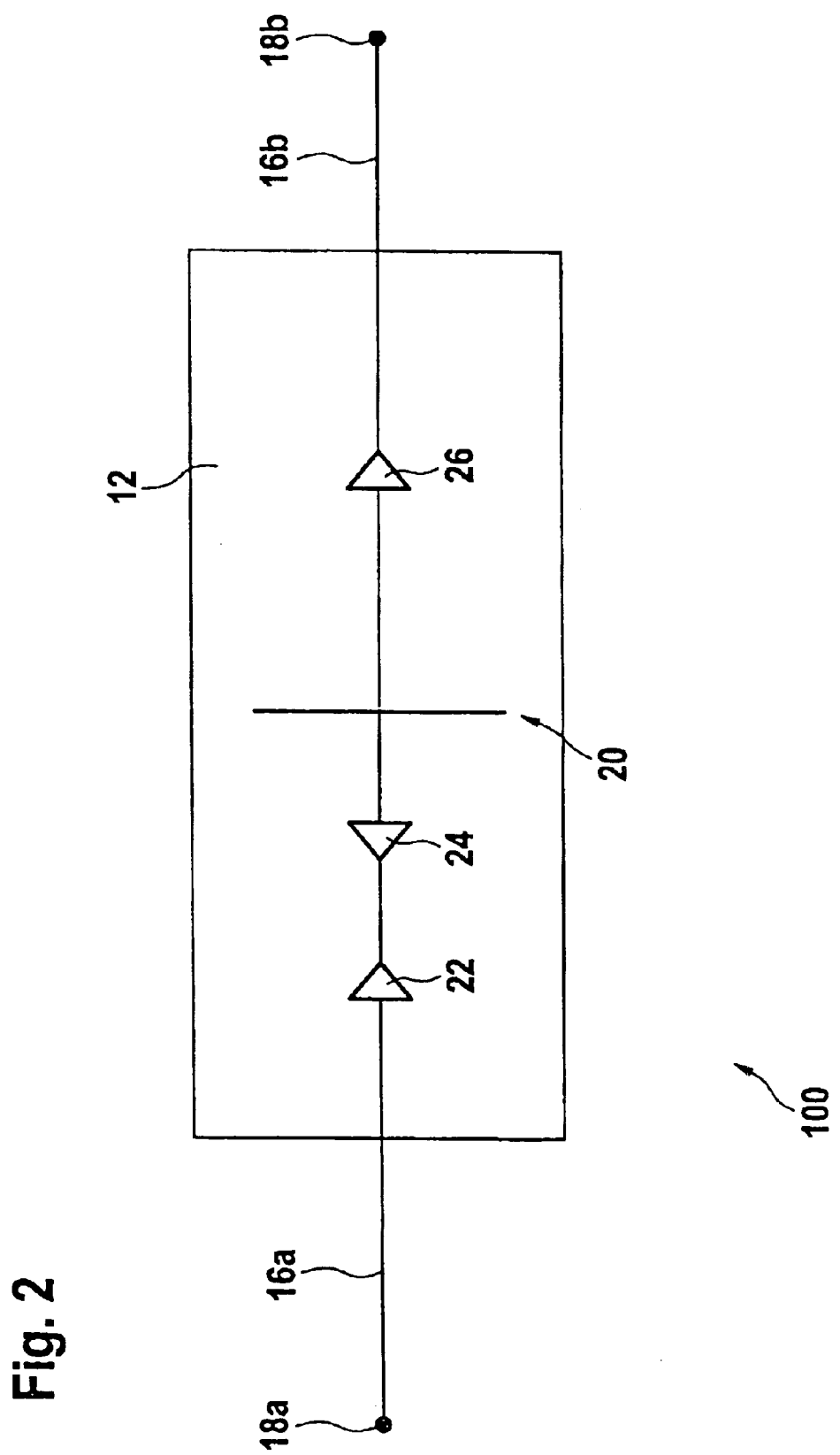
FIG. 2 shows a first embodiment of the element of the present invention.

FIG. 2 shows a first embodiment 100 of element 12. In embodiment 100, element 12 comprises a semi-transparent mirror, i.e., mirror 20. Light 22 propagates along patch-cord 16a toward mirror 20. Mirror 20 reflects 50% of light 22 back into patch-cord 16a as light 24, and lets 50% of light 22 travel through mirror 20 as light 26, which light travels along patch-cord 16b to connector 18b. Therefore, element 12, according to FIG. 2, provides transmission and reflection of incoming light, i.e., light 22. However, different ratios of transmission and reflection can be used.

Figure 3:
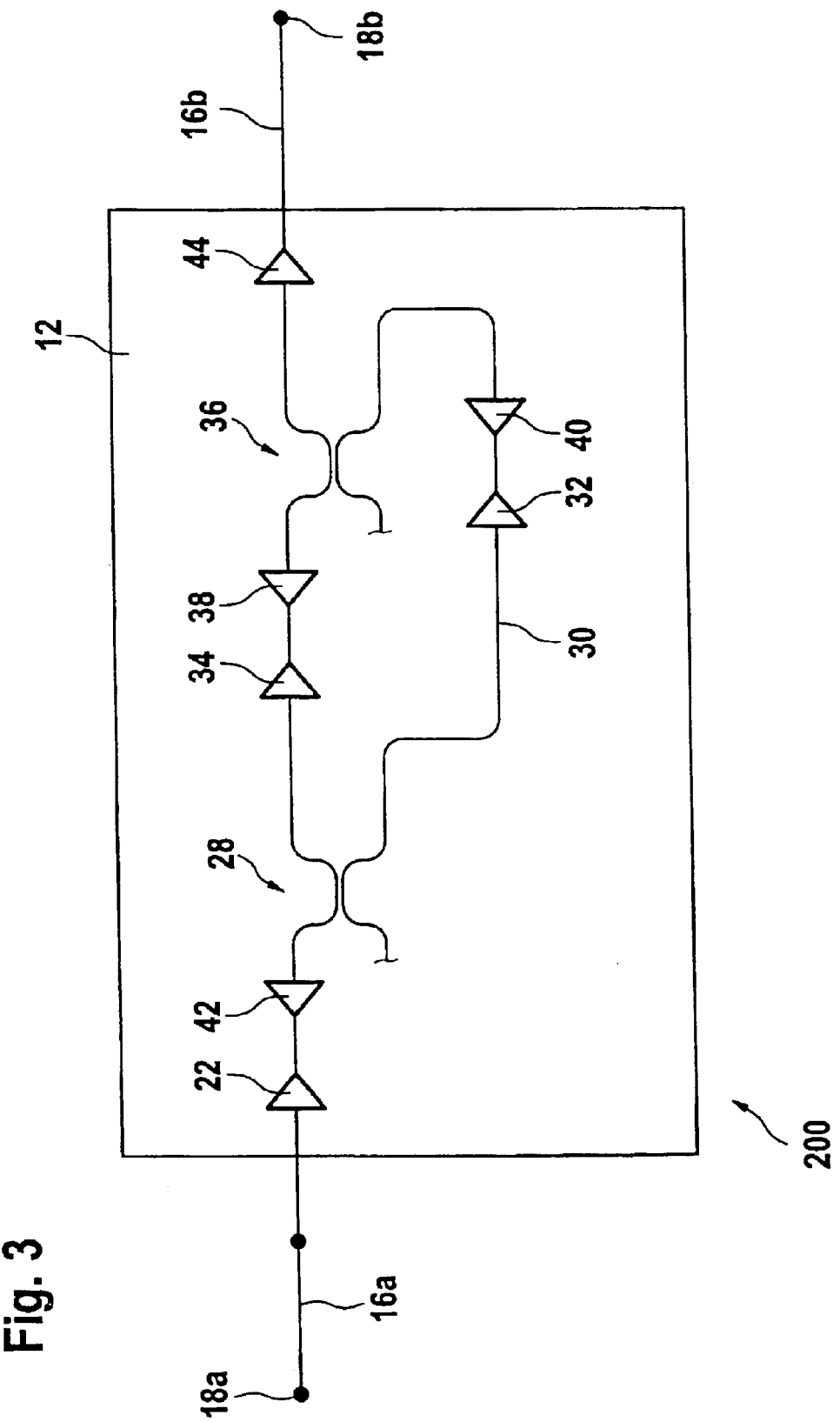
FIG. 3 shows a second embodiment of the element of the present invention.

FIG. 3 shows a second embodiment 200 of element 12. Element 12 of embodiment 200 comprises a first coupler, i.e., coupler 28, which is preferably a 3 dB coupler, but other couplers, such as 10 dB couplers, can be used instead. Coupler 28 lies in an initial path provided by patch-cord 16a of light 22. Coupler 28 couples out 50% of light 22 into a first path 30 as light 32. The other 50% travels along the initial path as light 34. Furthermore, element 12 comprises a second coupler, i.e., coupler 36, which couples light 32 partly back into the Initial path in reverse direction as light 38. Additionally, coupler 36 couples light 34 into first path 30, as light 40. Light 40 is partly coupled back into the initial path in reverse direction via coupler 28 as light 42. The part of light 34 not coupled out of the initial path by coupler 36 travels along patch-cord 16b to connector 18b as light 44. Therefore, element 12 in embodiment 200 provides light 44, which is a portion of light 22, in transmission at connector 18b, and provides light 42, which is also a portion of light 22, in reflection at connector 18a.

Furthermore, by adjusting couplers 28 and 36, e.g., by using 10 dB couplers or other couplers, it is possible to adjust a ratio of reflected light, i.e., light 42, to transmitted light, i.e., light 44.

Figure 4:
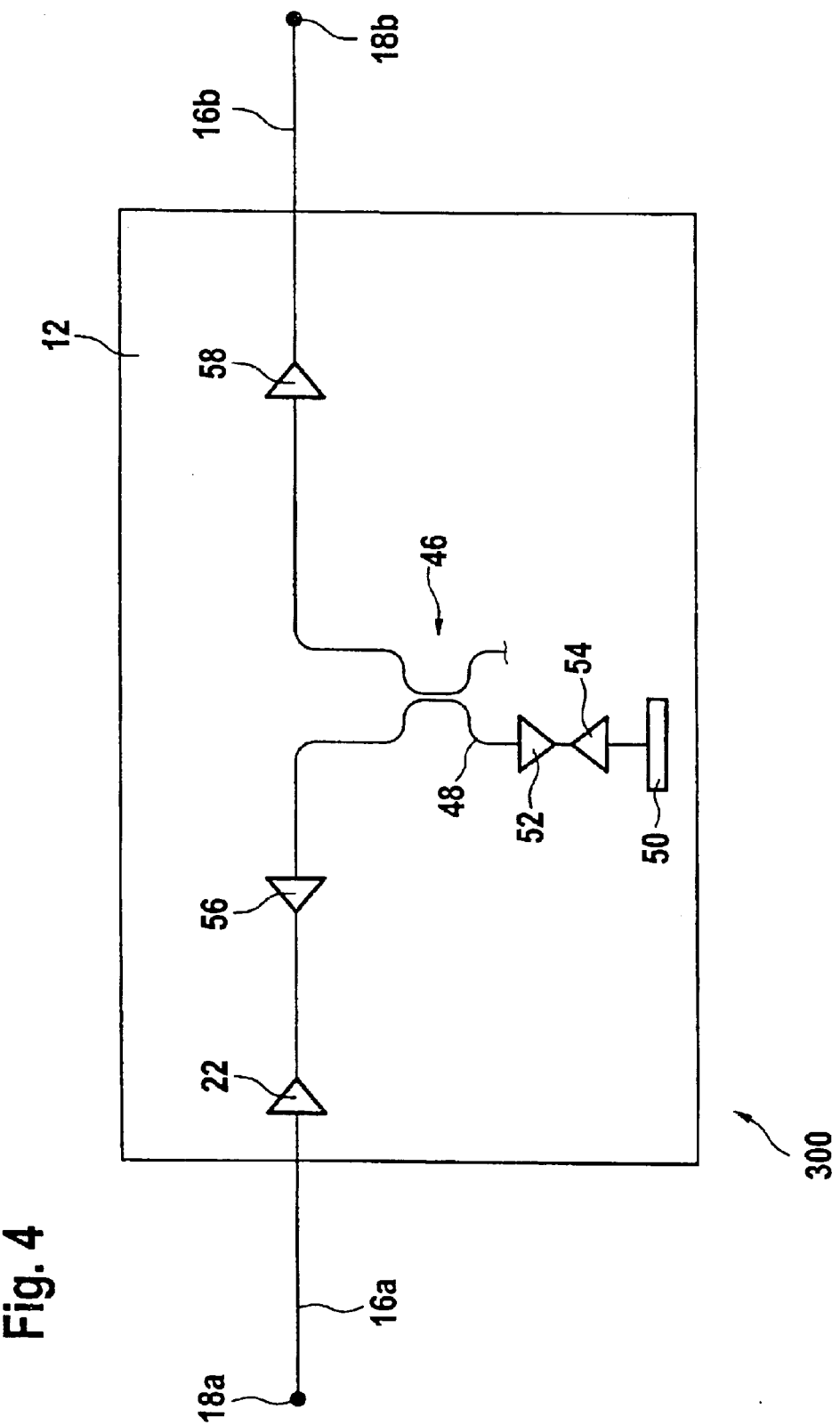
FIG. 4 shows a third embodiment of the element of the present invention.

FIG. 4 shows a third embodiment 300 of element 12. In embodiment 300 light 22 is partly coupled out by a coupler 46 into a first path 48 as light 52. At the end of first path 48 there is provided a mirror 50. Mirror 50 reflects light 52 in total as light 54. Subsequently, coupler 46 couples light 54 into the initial path, in reverse direction, as light 56 and into patch-cord 16b in a direction to connector 18b as light 58. Therefore, element 12 according to embodiment 300 provides a portion of light 22 in transmission at connector 18b, i.e., light 58, and a portion of light 22 in reflection at connector 18a, i.e., light 56.

Figure 5:
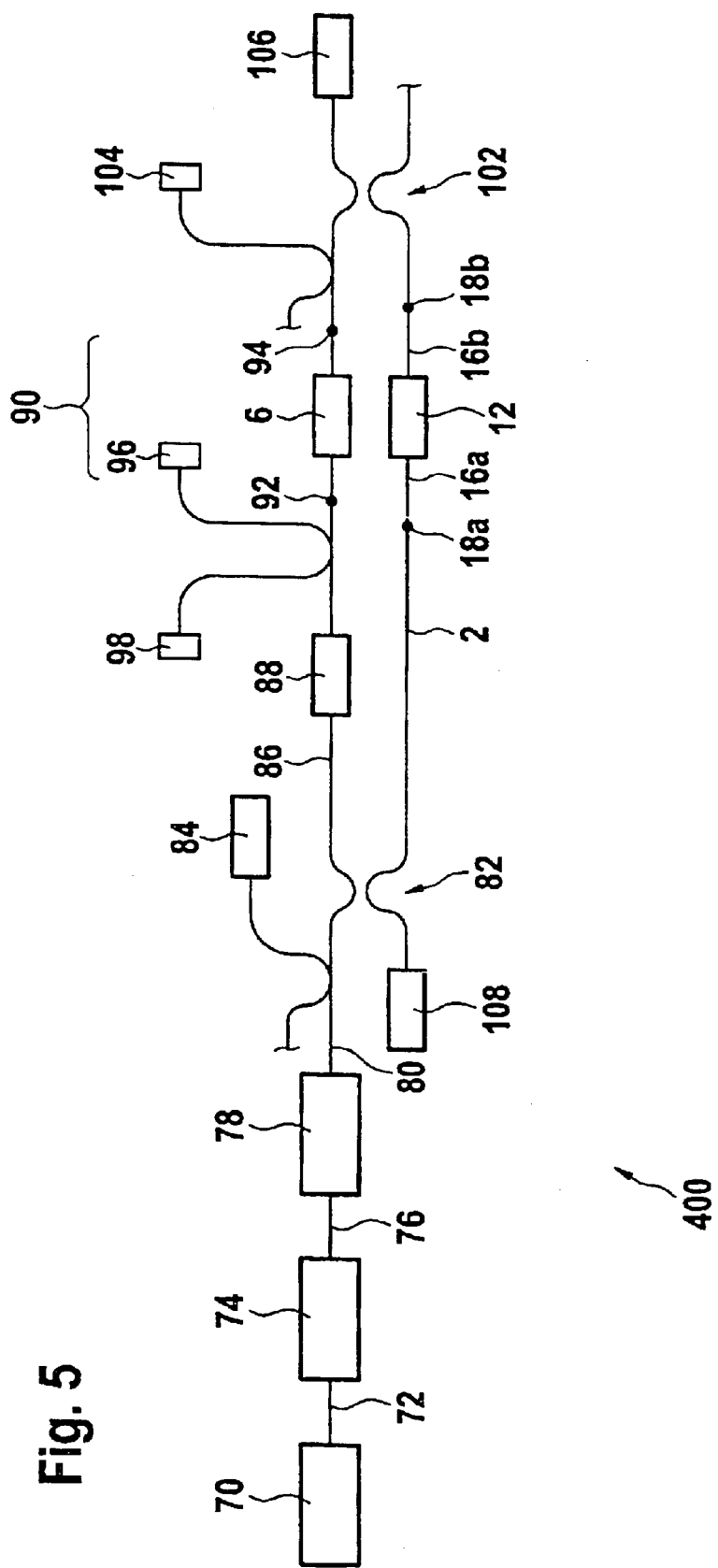
FIG. 5 shows a first measurement setup according to the present invention.

FIG. 5 shows a first embodiment 400 of a measurement setup according to the present invention. Measurement setup 400 contains a tunable light source 70 that provides a coherent laser beam 72 to a polarization controller 74 (which can be a Hewlett-Packard HP 8169A). Polarization controller 74 provides a polarization controlled coherent light beam 76 to an isolator 78. Optically connected with isolator 78 and receiving a coherent light beam, i.e., beam 80, from isolator 78 is a coupler 82, e.g., a 3 dB coupler. Also optically connected with isolator 78 and receiving beam 80 is a wavelength reference unit 84 (see also FIG. 6) to detect a wavelength of beam 80.

Reference arm 2 and a measurement arm 86 are connected to coupler 82. A switch 88 is provided in measurement arm 86 to cut measurement arm 86 for calibration purposes. Additionally, measurement arm 86 contains a seat 90 to receive DUT 6. Seat 90 has two connectors 92 and 94 to enable DUT 6 to be connected to measurement arm 86.

Between coupler 82 and seat 90 there is a detector 96 for measuring signal strength of a portion of beam 80 that is split by coupler 82 into measurement arm 86. Additionally, there is a detector 98 for measuring a signal strength of light being reflected by DUT 6.

Furthermore, measurement arm 86 is connected to a coupler 102, e.g., a 3 dB coupler. Between seat 90 and coupler 102 there is a detector 104 for measuring a signal strength of light transmitted through DUT 6.

A polarization diversity receiver 106 is connected to coupler 102 to detect a superimposed signal, that is a superposition o a signal transmitted by DUT 6 and a reference signal coupled in by coupler 102 from reference arm 2. The reference signal is coupled into reference arm 2 by coupler 82.

A polarization diversity receiver 108 is connected to coupler 82. Polarization diversity receiver 108 detects a superimposed signal, that is a superposition of a reflected signal from DUT 6 coupled in by coupler 82 from measurement arm 86 and a reflected reference signal coupled in from reference arm 2 coming from element 12.

For further details may be found in European Patent Application 00125089.3, which issued as European Patent No. EP 1 113 250 A1, the disclosure of which is incorporated herein by reference.

Figure 6:
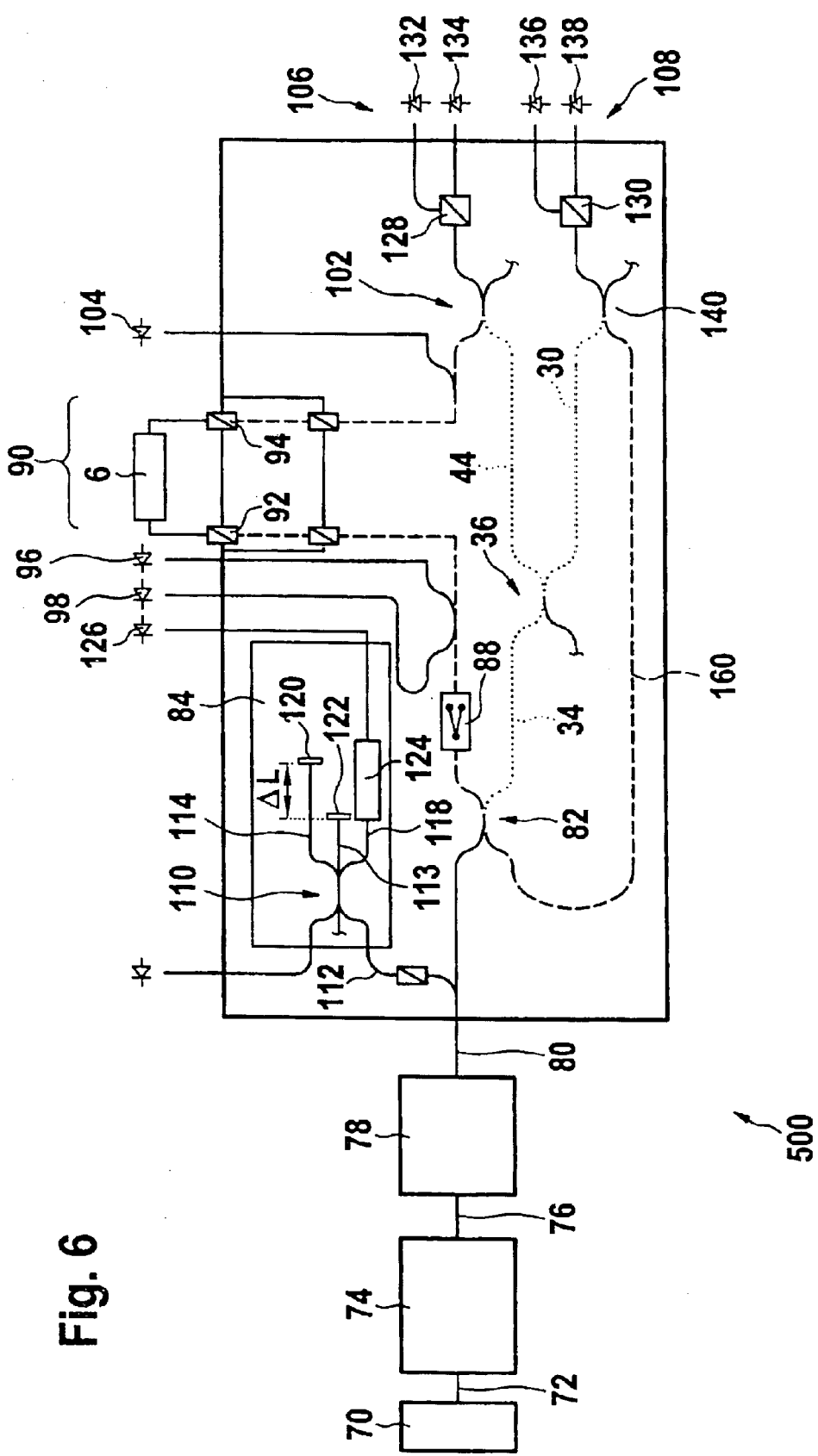
FIG. 6 shows a second measurement setup according to the present invention.

FIG. 6 shows a second embodiment 500 of a measurement setup according to the present invention. FIG. 6 also shows further details of wavelength reference unit 84. Wavelength reference unit 84 contains a six port coupler 110, which splits a beam 112 coupled out from beam 80 into three beams 114, 116 and 118. Beams 114 and 116 are directed onto Faraday mirrors 120 and 122. Faraday mirror 120 can be shifted to change a length of the path of beam 114. Furthermore, wavelength reference unit 84 contains a gas cell 124 connected with a power detector 126. A gas in gas cell 124 has a known absorption spectrum. With the help of power detector 126 and the known absorption spectrum of the gas in gas cell 124, it is possible to determine a wavelength of beam 80 very precisely.

Additionally, embodiment 500 shows polarization diversity receivers 106 and 108 in further detail. Both have polarization beam splitters 128 and 130 that are connected to power detectors 132, 134, 136 and 138.

Contrary to embodiment 400, in embodiment 500, element 12 is not connected as shown in embodiment 200. In embodiment 500, path 30 is not coupled into a reference arm directly as shown in embodiment 200. In embodiment 500, path 30 is coupled with a coupler 140 to superimpose a reference signal guided by path 30 with a reflected signal of path 160 directly in front of polarization diversity receiver 108. This advantageously avoids introduction of a reference signal on path 30 into the initial path of beam 80.

What is claimed is:

1. An apparatus, comprising:
   a coupler that receives light propagating along an initial path in a forward direction, and couples out (a) a first portion of said light into a first path, and (b) a second portion of said light into a second path; and
   an optical guide that receives said first portion, produces a third portion of said light from said first portion, and guides said third portion into said initial path in a reverse direction.

2. The apparatus of claim 1,
   wherein said coupler is a first coupler, and
   wherein said optical guide comprises a second coupler that receives said first portion via said first path and provides said third portion to said initial path.

3. A system, comprising:
   a measurement arm to receive a device under test (DUT);
   a transmission detector in optical contact to the measurement arm to detect a signal transmitted by said DUT;
   a reflection detector in optical contact with said measurement arm to detect a signal reflected by said DUT;
   a reference arm in optical contact with said transmission detector to provide a transmission reference signal to said transmission detector; and
   an apparatus, situated in said reference arm, in optical contact with said reflection detector to provide a reflection reference signal to said reflection detector, and a transmission reference to said transmission detector.

4. The system of claim 3, further comprising:
   a first coupler in optical contact with said measurement arm and said reference arm to provide a coherent light beam to said measurement arm and said reference arm; and
   a second coupler in optical contact with said measurement arm said reference arm and said transmission detector to superimpose the said signal transmitted by said DUT with said transmission reference signal, thus producing a superimposed signal, and to provide said superimposed signal to said transmission detector.

5. The system of claim 3,
   wherein at least one of said transmission detector or said reflection detector comprises a polarization beam splitter and that allocates light to a power detector; and
   wherein said power detector provides a signal representing detected power to an evaluation unit that evaluates said detected power for a determination of an optical property of said DUT.

6. The system of claim 3, further comprising:
   a seat for said DUT, situated in said measurement arm between a first coupler and a second coupler;
   a first power detector in optical contact with said first coupler, located between said first coupler and said seat, that measures a signal strength of a signal inputted into said DUT; and
   a second power detector in optical contact with said seat, located between said seat and said second coupler, that measures a signal strength of a signal transmitted by said DUT.

7. The system of claim 6, further comprising:
   a seventh power detector in optical contact with the seat, located between the third beam splitter and the seat, for measuring the signal strength of the signal reflected by the DUT.

8. An apparatus, comprising:
   a coupler that receives light propagating along an initial path in a forward direction, and couples out (a) a first portion of said optical light into a first path, and (b) a second portion of said light into a second path; and
   a mirror that reflects said first portion back to said coupler,
   wherein said coupler produces a third portion of said light from said reflected first portion and couples said third portion into said initial path in a reverse direction.

9. A method comprising:
   receiving reference light that is propagating along a reference path in a forward direction;
   transmitting a first portion of said reference light as a transmission reference;
   returning a second portion of said reference light to said reference path, in a reverse direction, as a reflection reference;
   employing said transmission reference and said reflection reference in an operation that yields data relating to transmission of light through a device under test (DUT) and reflection of light from said DUT; and
   analyzing said data to determine an optical property of said DUT.

10. A data carrier, comprising:
    a program for controlling a processor to analyze data to determine an optical property of a device under test DUT,
    wherein said data relates to transmission of light through said DUT and reflection of light from said DUT and is obtained during a measurement that employs a transmission reference and a reflection reference, and
    wherein said transmission reference and said reflection reference are provided by an apparatus that receives reference light that is propagating along a reference path in a forward direction, transmits a first portion of said reference light as said transmission reference, and returns a second portion of said reference light to said reference path, in a reverse direction, as said reflection reference.

* * * * *